(12) United States Patent
West et al.

(10) Patent No.: US 11,311,666 B1
(45) Date of Patent: Apr. 26, 2022

(54) MODULAR WEARABLE MEDICAMENT DELIVERY DEVICE AND METHOD OF USE THEREOF

(71) Applicant: Fresenius Kabi Deutschland GmbH, Bad Homburg (DE)

(72) Inventors: Sharon D. West, Elkins Park, PA (US); Justin E. Bechstein, Philadelphia, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/178,782

(22) Filed: Feb. 18, 2021

(51) Int. Cl.
*A61M 5/168* (2006.01)
*A61M 5/142* (2006.01)

(52) U.S. Cl.
CPC .................. *A61M 5/14248* (2013.01); *A61M 2005/14252* (2013.01); *A61M 2230/201* (2013.01); *A61M 2230/208* (2013.01); *A61M 2230/30* (2013.01); *A61M 2230/50* (2013.01)

(58) Field of Classification Search
CPC .......... A61M 5/14248; A61M 5/14244; A61M 2005/14252; A61M 2005/14268
See application file for complete search history.

(56) References Cited

U.S. PATENT DOCUMENTS

| | | | |
|---|---|---|---|
| 5,620,312 A * | 4/1997 | Hyman | A61M 5/142 417/474 |
| 5,897,530 A | 4/1999 | Jackson | |
| 6,589,229 B1 | 7/2003 | Connelly et al. | |
| 7,147,615 B2 | 12/2006 | Wariar et al. | |
| 8,088,096 B2 | 1/2012 | Lauchard et al. | |
| 9,061,097 B2 | 6/2015 | Holt et al. | |
| 10,569,014 B2 | 2/2020 | Hanson et al. | |
| 10,583,245 B2 | 3/2020 | McCullough et al. | |
| 10,625,018 B2 | 4/2020 | Destefano et al. | |
| 10,646,664 B2 | 5/2020 | Lee et al. | |
| 10,682,474 B2 | 6/2020 | Ring et al. | |
| 10,758,683 B2 | 9/2020 | Gibson et al. | |
| 2002/0123735 A1 | 9/2002 | Rake et al. | |
| 2002/0123740 A1 | 9/2002 | Flaherty et al. | |
| 2003/0009131 A1 | 1/2003 | Van Antwerp et al. | |
| 2003/0187395 A1 | 10/2003 | Gabel et al. | |
| 2011/0105872 A1 | 5/2011 | Chickering, III et al. | |
| 2012/0010594 A1 | 1/2012 | Holt et al. | |
| 2012/0310175 A1 | 12/2012 | Vedrine et al. | |

(Continued)

FOREIGN PATENT DOCUMENTS

EP 2796157 B1 9/2016
WO 2014143770 A1 9/2014

(Continued)

OTHER PUBLICATIONS

U.S. Appl. No. 17/178,799, filed Feb. 18, 2021.
U.S. Appl. No. 17/178,795, filed Feb. 18, 2021.

*Primary Examiner* — Laura A Bouchelle
(74) *Attorney, Agent, or Firm* — Goodwin Procter LLP (57) ABSTRACT

A medicament delivery device and method of use thereof. The device includes a sensor module and an injector module. The injector module is adapted to (i) be coupled to the sensor module during injection of a cannula and a needle into subcutaneous tissue and during delivery of the medicament and (ii) be removed from the sensor module after the delivery of the medicament.

20 Claims, 5 Drawing Sheets

(56) References Cited

U.S. PATENT DOCUMENTS

| | | |
|---|---|---|
| 2014/0100522 A1 | 4/2014 | Nie et al. |
| 2015/0374919 A1 | 12/2015 | Gibson |
| 2016/0038689 A1 | 2/2016 | Lee et al. |
| 2016/0199574 A1 | 7/2016 | Ring et al. |
| 2016/0296704 A1 | 10/2016 | Gibson |
| 2016/0354555 A1 | 12/2016 | Gibson et al. |
| 2017/0147787 A1 | 5/2017 | Albrecht et al. |
| 2017/0182253 A1 | 6/2017 | Folk et al. |
| 2017/0361015 A1 | 12/2017 | McCullough |
| 2017/0368260 A1 | 12/2017 | McCullough et al. |
| 2018/0001021 A1 | 1/2018 | Wu et al. |
| 2018/0021508 A1 | 1/2018 | Destefano et al. |
| 2018/0028747 A1 | 2/2018 | Hanson et al. |
| 2018/0036476 A1 | 2/2018 | McCullough et al. |
| 2018/0085517 A1 | 3/2018 | Laurence et al. |
| 2018/0133447 A1 | 5/2018 | McAllister et al. |
| 2018/0256823 A1 | 9/2018 | Nazzaro et al. |
| 2018/0304014 A1 | 10/2018 | Knudsen et al. |
| 2019/0022306 A1 | 1/2019 | Gibson et al. |
| 2019/0050375 A1 | 2/2019 | Fitzgibbon et al. |
| 2019/0060562 A1 | 2/2019 | Olivas et al. |
| 2019/0134296 A1 | 5/2019 | Barbedette et al. |
| 2019/0143043 A1 | 5/2019 | Coles et al. |
| 2019/0151544 A1 | 5/2019 | Stonecipher |
| 2019/0167908 A1 | 6/2019 | Fitzgibbon et al. |
| 2019/0192766 A1 | 6/2019 | Stonecipher |
| 2019/0247579 A1 | 8/2019 | Damestani et al. |
| 2019/0275235 A1* | 9/2019 | Barmaimon ...... A61M 5/14248 |
| 2019/0275241 A1 | 9/2019 | Ring et al. |
| 2019/0307958 A1* | 10/2019 | Yang .................. A61B 5/1118 |
| 2019/0328965 A1 | 10/2019 | Moberg |
| 2019/0365986 A1 | 12/2019 | Coiner et al. |
| 2019/0381238 A1 | 12/2019 | Stonecipher et al. |
| 2020/0069875 A1* | 3/2020 | Nazzaro ............... A61M 5/1723 |
| 2020/0179609 A1 | 6/2020 | Tan-Malecki et al. |
| 2020/0188585 A1 | 6/2020 | Petisce et al. |
| 2020/0253525 A1 | 8/2020 | Zhang et al. |
| 2021/0069411 A1* | 3/2021 | Demers .................. A61M 5/14 |

FOREIGN PATENT DOCUMENTS

| | | |
|---|---|---|
| WO | 2015187797 A1 | 12/2015 |
| WO | 2016100055 A1 | 6/2016 |
| WO | 2016130679 A2 | 8/2016 |
| WO | 2016133947 A1 | 8/2016 |
| WO | 2016145094 A2 | 9/2016 |
| WO | 2016130679 A3 | 11/2016 |
| WO | 2017120178 A1 | 7/2017 |
| WO | 2017200989 A1 | 11/2017 |
| WO | 2018081234 A1 | 5/2018 |
| WO | 2018151890 A1 | 8/2018 |
| WO | 2018164829 A1 | 9/2018 |
| WO | 2018165499 A1 | 9/2018 |
| WO | 2018183039 A1 | 10/2018 |
| WO | 2018226515 A1 | 12/2018 |
| WO | 2018226565 A1 | 12/2018 |
| WO | 2018236619 A1 | 12/2018 |
| WO | 2018237225 A1 | 12/2018 |
| WO | 2019014014 A1 | 1/2019 |
| WO | 2019018169 A1 | 1/2019 |
| WO | 2019022950 A1 | 1/2019 |
| WO | 2019022951 A1 | 1/2019 |
| WO | 201932101 A1 | 2/2019 |
| WO | 2019032482 A2 | 2/2019 |
| WO | 2019070472 A1 | 4/2019 |
| WO | 2019070552 A1 | 4/2019 |
| WO | 2019074579 A1 | 4/2019 |
| WO | 2019089178 A1 | 5/2019 |
| WO | 2019090303 A1 | 5/2019 |
| WO | 2019143753 A1 | 7/2019 |
| WO | WO-2020112515 A1 | 6/2020 |

* cited by examiner

MODULAR WEARABLE MEDICAMENT DELIVERY DEVICE AND METHOD OF USE THEREOF

TECHNICAL FIELD

The present disclosure generally relates to drug delivery devices and, more particularly, a drug delivery device capable of being worn by a patient while the drug delivery device delivers a drug to the patient.

BACKGROUND

Delivery of medicaments, e.g., liquid drugs, to a patient via injection using a needle or syringe is well-known. More recently, devices that automate the delivery of medicaments have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the medicament into the body of the patient at one or more scheduled times. For example, a device may be configured to deliver a medicament over the span of 45 minutes, with delivery beginning 27 hours after the device has been activated and applied to a patient (to ensure that the medicament is not delivered sooner than 24 hours after a medical procedure or treatment). These devices improve upon manual methods by obviating the need for the patient to inject themselves with the medicament (which carries heightened risks of the patient improperly administering the injection or injecting the medicament at an inappropriate time) or to return to a medical facility for one or more injections by a technician or medical professional.

Figure 1:
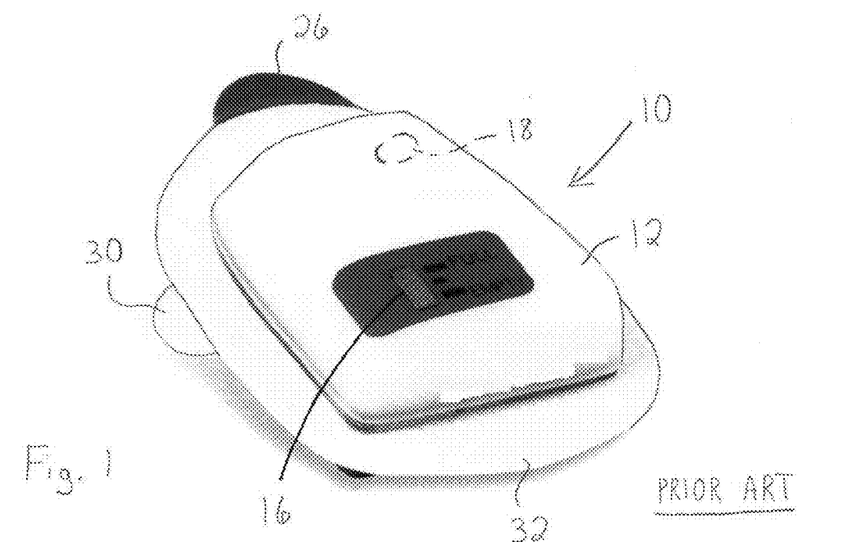
FIG. 1 is a schematic, perspective view of a known medicament delivery device.
Figure 2:
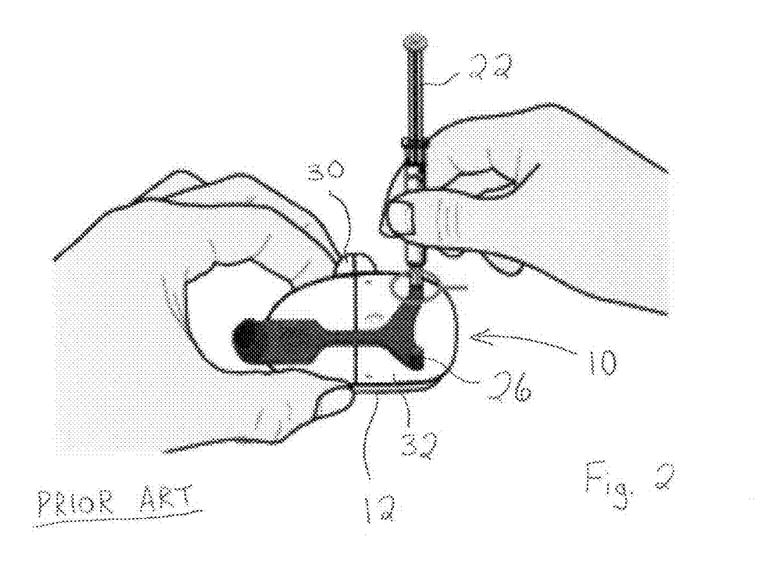
FIG. 2 is a schematic, bottom view of the device of FIG. 1 being filled with a medicament.
Figure 3:
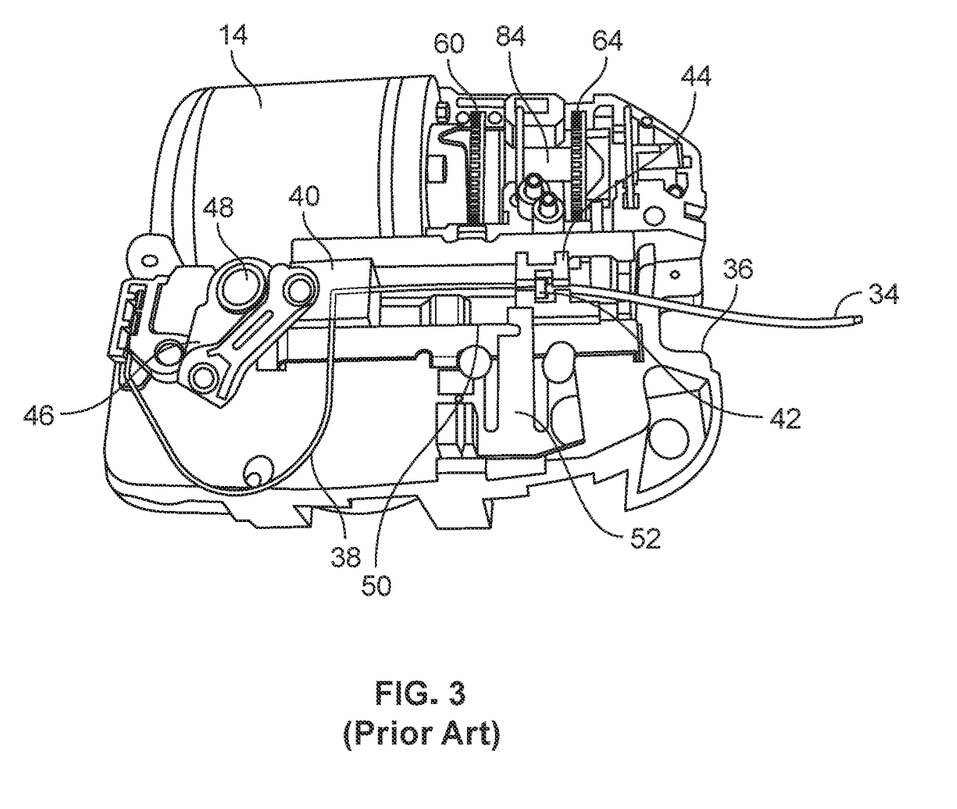
FIGS. 3 and 4 are images of functional components of the device of FIG. 1 in which an exterior housing of the device has been removed.
Figure 4:
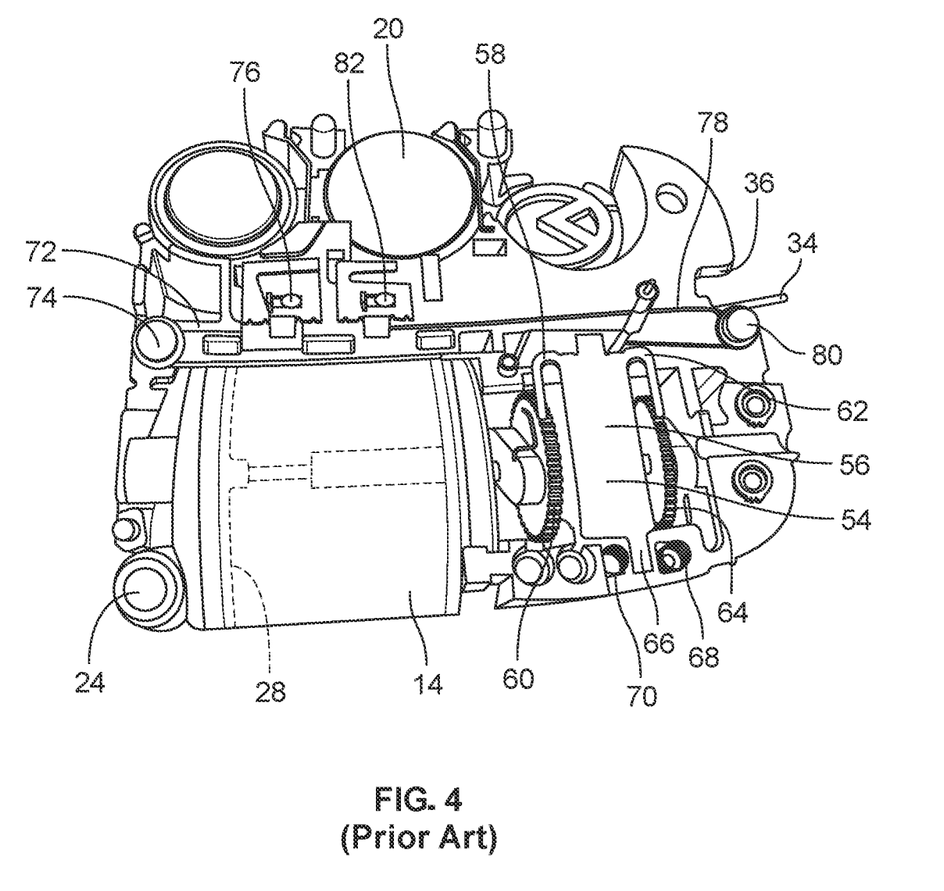

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a medicament to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the medicament to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a medicament delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. A battery 20 provides power to the status light 18 and the other electrical components of the device 10.

The medicament is injected into the reservoir 14 using a (typically pre-filled) syringe 22 via a port 24 incorporated into the bottom or underside of the housing 12 (FIG. 4) and fluidly connected to the reservoir 14. FIGS. 1 and 2 illustrate an applicator 26 that is removably associated with the underside of the housing 12 and used in combination with the syringe 22 to fill the reservoir 14 via the port 24. The medicament is most typically injected into the reservoir 14 by a medical professional immediately before the device 10 is secured to the patient to ensure that the proper medicament is supplied, along with the proper amount.

A piston or plunger 28 (FIG. 4) positioned within the reservoir 14 is moved (from left to right, in the orientation of FIG. 4) as the space within the reservoir 14 is filled by the inflowing medicament. Movement of the piston 28 into its final position (when the reservoir 14 has been filled with the appropriate amount of the medicament) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the medicament out of the reservoir 14 (e.g., 27 hours after the device 10 has been activated) will cause the medicament to move into the needle 38 (via the proximal end of the needle 38), through the needle 38 (to its distal end), and into the cannula 34. The medicament is then delivered to the patient (e.g., over the course of a 45-minute session) via the distal end of the cannula 34 positioned within the skin.

As for the mechanism by which the medicament is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 allow the lever 54 to stay electrically coupled to the electrical contacts 76 and 82 (which are electrically coupled to the above-referenced printed circuit board) as the lever 54 pivots about the pivot point 56.

At the designated time (e.g., 27 hours after the device 10 has been activated), the controller provides commands that cause the lever 54 to be alternately pivoted about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are contained within a single part and are associated with a common shaft 84 (FIG. 3), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the medicament out of the reservoir 14 via the proximal end of the needle 38. As described above, the medicament will flow through the needle 38, into and through the cannula 34, and into the body of the patient.

After the medicament has been delivered (e.g., over the course of a 45-minute session), the controller alerts the patient via a visual cue from the status light 18 and/or an audible cue from the buzzer that medicament delivery is complete. Subsequently, the patient removes the device 10 from their skin and discards the device 10.

While devices of the type described above have proven adequate, there is room for improvement of them. For example, existing devices have a relatively large profile that can inhibit patient activities and/or cause embarrassment. Accordingly, patients often seek to minimize the time that existing devices are worn, which can limit the time during which data can be collected from the devices.

SUMMARY

Applicants have invented an improved wearable delivery device that facilitates increased collection of biometric data from patients. Although some biometric data measurement is helpful during delivery of a medicament, a significant amount of useful data is available post-injection (e.g., related to patient acceptance and/or reaction to the medicament, as well as other general biometric data related to patient health and otherwise). The ability to measure such post-injection data is limited, however, to the amount of time patients are willing to wear the device. As mentioned above, the large profile of the device often motivates patients to wear devices for as short a time as possible. However, the components of the device needed for biometric sensing have a significantly smaller profile, than the components required for cannula injection and drug delivery. As such, Applicants have invented a device that allow the larger profile components to be decoupled from the biometric sensing elements, thereby allowing the larger profile components to be removed from the patients once they are no longer needed, while leaving the biometric sensing elements behind. This enables collection of biometric patient data over a far longer period, which can have significant health and other benefits.

In general, in one an aspect, embodiments of the invention relate to a$_{[GM1]}$ medicament delivery device including a sensor module having a sensor housing with one or more sensors disposed in the sensor housing, and an adhesive patch adapted for connecting the sensor module to a skin surface. An injector module includes an injector module housing, and a reservoir disposed in the injector module housing and adapted to be filled with a medicament to be delivered to a patient. The injector module also includes a cannula adapted to (i) fluidically connect with the reservoir and (ii) pass into a subcutaneous tissue, and a needle initially disposed in a lumen defined by the cannula and is adapted to pass into the subcutaneous tissue. The injector module also includes a coupling mechanism adapted to couple the injector module to the sensor module. The injector module is adapted to (i) be coupled to the sensor module during injection of the cannula and the needle into the subcutaneous tissue and during delivery of the medicament and (ii) be removed from the sensor module after the delivery of the medicament.

One or more of the following features may be included. The at least one sensor may include a temperature sensor, an accelerometer, a gyroscope, a pulse oximeter, a blood pressure sensor, a hydration sensor, a pH sensor, glucose sensor, and/or a UV exposure sensor. The at least one sensor may be disposed on a bottom surface of the sensor module and is configured to be in contact with the skin surface when the adhesive patch is connected thereto.

The coupling mechanism may include a latch. The sensor module may define a recess adapted to mate with the latch. The coupling mechanism may include a push button adapted to move the latch between an engaged position and a disengaged position. The push button may extend through a portion of the injector module housing. The push button may be adapted to initiate cannula insertion when the push button is pressed into a depressed position.

The injector module may include an injector timer, and the push button may be adapted to start the injection timer when the push button is pressed into a depressed position. The push button may be adapted to move from the depressed position to a released position after a predetermined time is measured by the injector timer.

The push button may be adapted to move the latch to the disengaged position when the push button is in the released position, thereby uncoupling the injector module from the sensor module.

The sensor housing of the sensor module may define a needle port. The cannula may be adapted to pass through the needle port of the sensor module. The needle may be adapted to pass through the needle port. The injector module may be adapted to be removed from the sensor module after withdrawal of the cannula and the needle from the subcutaneous tissue.

The needle may include a sensing component.

In another aspect, embodiments of the invention relate to a method for delivering a medicament, the method including connecting to a skin surface a medicament delivery device including an injector module coupled to a sensor module including at least one sensor, with the injector module including a reservoir containing the medicament. The medicament is delivered from the injector module into a subcutaneous tissue. After delivery of the medicament, the injector module is removed from the sensor module while leaving the sensor module in contact with the skin surface.

One or more of the following features may be included. The injector module may include a cannula in fluidic communication with the reservoir, and delivering the medicament may include passing the cannula into the subcutaneous tissue.

The cannula may be left in the subcutaneous tissue after delivery of the medicament. The injector module may include a needle disposed in a lumen in the cannula, and delivering the medicament may include piercing the skin surface with the needle prior to passing the cannula into the subcutaneous tissue. The needle may include a sensing component, and a biometric component may be monitored with the needle while the needle contacts the skin.

A biometric parameter may be monitored with the sensor module, e.g., after the injector module is removed. The biometric parameter may be temperature, oxygen level, blood pressure, hydration, pH, glucose, and/or UV exposure.

The injector module may include a coupling mechanism adapted to couple the injector module to the sensor module. The coupling mechanism may include a latch. The sensor module may define a recess adapted to mate with the latch.

The coupling mechanism may include a push button adapted to move the latch between an engaged position and a disengaged position. Delivering the medicament may include pushing the push button into a depressed position. Pushing the push button into the depressed position may initiate insertion of a cannula into the subcutaneous tissue.

The injector module may include an injector timer, and delivering the medicament may include pushing the push button into a depressed position to start the injection timer.

Delivering the medicament may include the push button moving to a released position after a predetermined time measured by the injector timer. Moving the push button to the released position may move the latch to the disengaged position, thereby uncoupling the injector module from the sensor module.

The medicament may include pegfilgrastim.

These and other objects, along with advantages and features of embodiments of the present invention herein disclosed, will become more apparent through reference to the following description, the figures, and the claims. Furthermore, it is to be understood that the features of the various embodiments described herein are not mutually exclusive and can exist in various combinations and permutations.

BRIEF DESCRIPTION OF DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

It is contemplated that apparatus, systems, methods, and processes of the claimed invention encompass variations and adaptations developed using information from the embodiments described herein. Adaptation and/or modification of the apparatus, systems, methods, and processes described herein may be performed by those of ordinary skill in the relevant art and are considered to be within the scope of the disclosed invention.

It should be understood that the order of steps or order for performing certain actions is immaterial, so long as the invention remains operable. Moreover, two or more steps or actions may be conducted simultaneously.

Embodiments of the invention include medicament delivery devices that include a combination of an injector module and a sensor module. This configuration enables removal of the injector module after delivery of a medicament, while leaving in place a low-profile sensor housing. This configuration provides the advantage of enabling sensing one or more biometric parameters for days after treatment, e.g., tracking temperature to catch febrile neutropenia. Sensors that may be included in the device are, e.g., thermometers, accelerometers, gyroscopes, pulse oximeters, blood pressure sensors, hydration sensors, pH sensors, glucose sensors, and UV exposure sensors. By incorporating the sensor into a separable module, the user needs to wear only a minimal patch for biometric sensing after the infusion is complete to continue health monitoring, The device thereby enables performing two related functions in a single application.

Figures 5A, 5B:
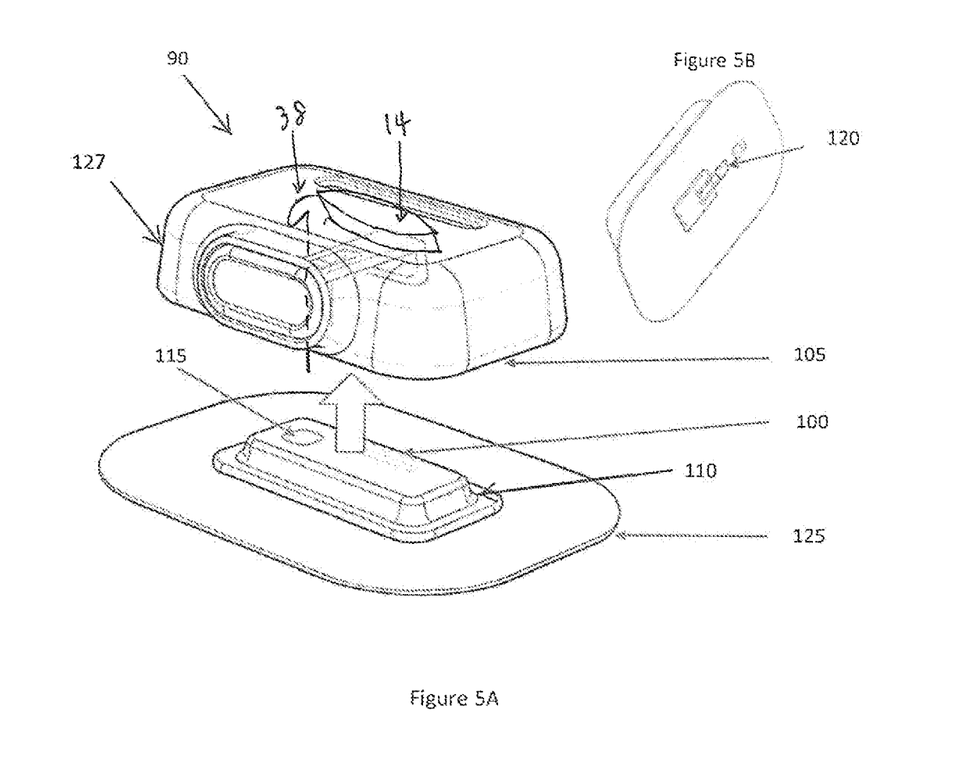
FIG. 5A is a schematic, perspective view of a medicament delivery device having an injector module and a sensor module, in accordance with an embodiment of the invention.
FIG. 5B is a schematic, perspective view of the sensor module of the medicament delivery device of FIG. 5A.

Referring to FIGS. 5A and 5B, a medicament delivery device 90 in accordance with embodiments of the invention includes a sensor module 100 and an injector module 105. The sensor module 100 includes a sensor housing 110. The sensor housing may define a needle port 115. A sensor 120 can be disposed in or on the sensor housing 110. The sensor 120 may be configured to be placed directly on the patient's skin, or it may be disposed within its own housing. Either option may be available for a particular sensor, e.g., a temperature sensor may be configured to be placed in direct skin contact during use, or it may be sufficiently sensitive to be separated from the skin while still maintaining thermal contact with the skin. An accelerometer, on the other hand, is unlikely to be placed in direct skin contact.

An adhesive patch 125 is disposed on a bottom surface of the sensor module 100. The adhesive patch is adapted for connecting the sensor module to a skin surface during use, i.e., it includes an adhesive that causes the adhesive pad (and, hence, the sensor module) to adhere to the body. The adhesive patch may define an opening for the sensor if contact to the skin by the sensor is required. Alternatively, if the sensor does not require skin contact, e.g., an accelerometer, an opening in the adhesive patch may not be required.

In various embodiments, the injector module 105 includes an injector module housing 127. The reservoir 14 (described above) is disposed in the injector module housing, with the reservoir 14 being adapted to be filled with a medicament to be delivered to a patient. The cannula 34 (described above) is adapted to be fluidically connected to the reservoir 14. In an embodiment, the cannula 34 is also adapted to pass through the needle port 115 of the sensor module 100 and into a subcutaneous tissue. The needle 38 (described above) is initially disposed in a lumen defined by the cannula 34 and adapted to pass through the needle port and into the subcutaneous tissue. In some embodiments (not shown), the cannula 34 may be adapted to pass to a side of the sensor module 100 and through a pass-through access hole defined by the adhesive patch 125.

Figure 6A:
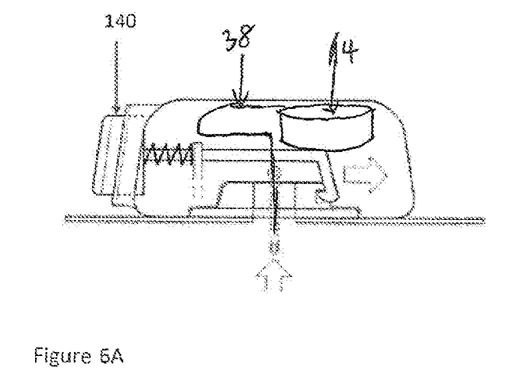
FIGS. 6A and 6B are schematic, side views of the medicament delivery device of FIG. 5A.
Figure 6B:
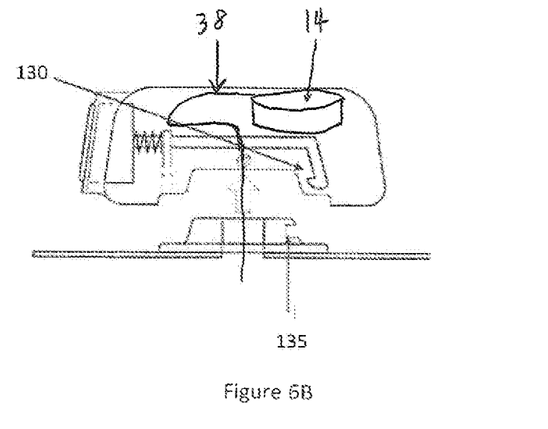

Referring to FIGS. 6A and 6B, in various embodiments, the injector module includes a coupling mechanism, such as a latch 130, adapted to couple the injector module to the sensor module. In general, in other embodiments, any coupling technique can be used, e.g., interference fit, threaded connection, interlocking components, etc. The injector module 105 is adapted to be coupled to the sensor module 110 during injection of the cannula 34 and the needle 38 into the subcutaneous tissue and during delivery of the medicament. In some embodiments, the injector module 105 remains coupled to the sensor module 100 during some or all of the following: (i) delivery of the cannula 34 and needle 38 into the subcutaneous tissue, (ii) partial retraction of the needle 38 from the cannula 34, and (iii) full delivery of the medicament to the patient (e.g., until the reservoir 14 is empty or other completion of dosage). The injector module 105 is also adapted to be removed from the sensor module 100 after the delivery of the medicament and withdrawal of the cannula 34 and the needle 38 from the subcutaneous tissue. In some embodiments, the injector module 105 includes both the cannula 34 and the needle 38 and removal of the injector module 105 leaves only the sensor module 100 attached to the patient. In other embodiments, the components can be distributed between the injector module 105 and the sensor module 100 differently, such that one or both of the cannula 34 and/or needle 38 can remain attached to the patient (e.g., proximate the sensor module 100) upon removal of the injector module 105. In some embodiments, the needle 38 may include a sensing component, and may be used as a sensor while it remains in contact with the skin the patient. In other embodiments, the injector module may be used to inject a cannula 34 as well as a separate sensor lead.

In some embodiments, the sensor module defines a recess 135 adapted to mate with the latch 130. The coupling mechanism may include a spring-loaded push button 140 adapted to move the latch between an engaged position and a disengaged position. In the engaged position, the injector module 105 is connected to the sensor module 100 by the latch being disposed in the recess. In some instances, this is the position of the modules 100, 105 during delivery of a medicament. In the disengaged position, the latch 130 is removed from the recess 135, thereby uncoupling the injector module 105 from the sensor module 100, so that that the injector module 105 may be removed from the sensor module 100. The push button 140 may extend through a portion of the injector module housing. The push button 140 may be adapted to initiate cannula insertion when the push button 140 is pressed into a depressed position. In other embodiments, the injector module 105 and sensor module 100 can have other corresponding structure to enable attachment and detachment. As a few examples, the structure can include a snap connection, a hook and loop connection, an interference fit connection, a magnetic connection, an adhesive, a tear-away strip, a bayonette connection, or a ¼ turn connection.

The injector module 105 may include an injector timer (not shown). The push button 140 (or other attachment structure) may be adapted to start the injection timer when the push button 140 is pressed into the depressed position. Furthermore, the push button 140 may be adapted to move from the depressed position to a released position after a predetermined time is measured by the injector timer. The predetermined time can be correlated to medicament delivery to the patient. For example, the predetermined time can be equal to (or within some percentage of) the amount of time required to complete a desired medicament dosage.

Figure 7A:
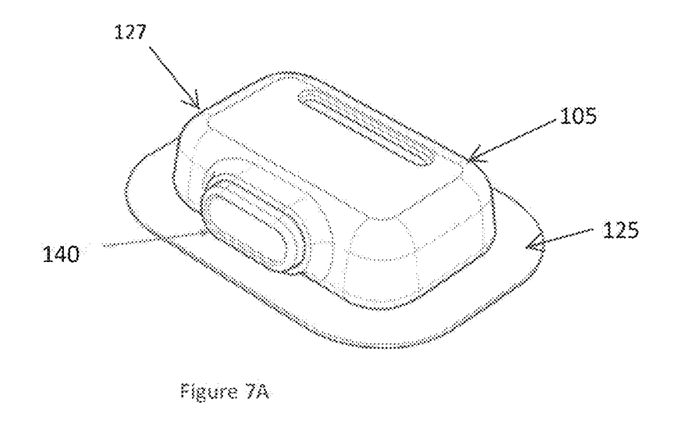
FIG. 7A is a schematic, perspective view of the injector module of the medicament delivery device of FIG. 5A.
Figure 7B:
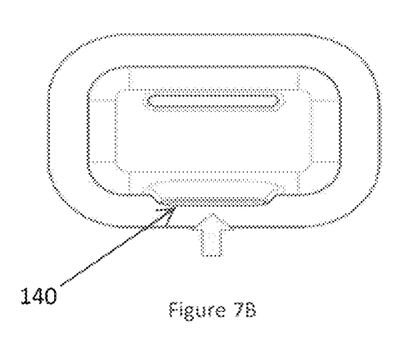
FIGS. 7B and 7C are schematic top views of the injector module of FIG. 7A.
Figure 7C:
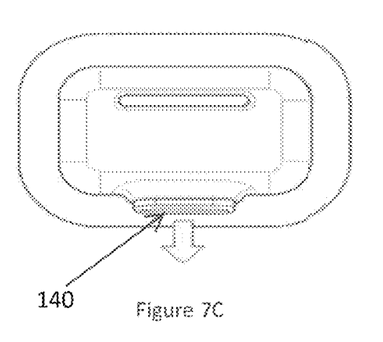

Referring to FIGS. 7A-7C, the push button 140 may be the single point of interface that controls cannula insertion (including optionally starting a timer) and removal of the injector module from the sensor module. For example, referring to FIG. 7B, pressing the button after application (e.g., by the patient or health care personnel) begins cannula insertion and the injection timer, with the button staying "inside" throughout a pre-designated time.

Referring to FIG. 7C, upon completion of injection, the push button 140 can be configured to protrude from the injector module housing 127 to indicate that the injection is complete. In other embodiments, other visual indicators beyond an extruding button can be used (e.g., visual, audible, and/or haptic cues) can be generated upon expiration of the predetermined time. In some embodiments, generation of the visual cue can also correlate with unlocking the injector module 105 from the sensor module 100. For example, the button 140 extruding can result in the unlocking of the latch 130 between the injector and sensor modules. In some such embodiments, pressing the exposed button 130 may mechanically release the injector module 105 from the sensor module 110.

Exemplary dimensions of the medicament delivery device are provided below:

TABLE 1

Exemplary parameters for medicament delivery device.

| Parameter | Low | Typical | High |
|---|---|---|---|
| Injector Module Housing Length L (mm) | 25 | 50 | 75 |
| Injector Module Housing Width W (mm) | 20 | 40 | 60 |
| Injector Module Housing Height H (mm) | 6 | 12 | 18 |
| Sensor Module Housing L (mm) | 25 | 50 | 75 |
| Sensor Module Housing W (mm) | 20 | 40 | 60 |
| Sensor Module Housing H (mm) | 6 | 12 | 18 |

In accordance with various embodiments of the invention, a medicament may be delivered to a patient as follows. The medicament delivery device 90 may be connected to a skin surface of a patient, e.g., with the adhesive patch. As described above, the medicament delivery device 90 may include the injector module 105 coupled to the sensor module 100 that includes a sensor. The medicament is disposed in the reservoir 14 of the injector module 105. The medicament is delivered from the injector module 105 into a subcutaneous tissue. For example, the needle 38 disposed in the cannula 34 may piece the skin surface and the cannula 34 may be passed through the needle port 115 of the sensor module 105 into the subcutaneous tissue. The medicament may then be delivered through the cannula 34. After delivery of the medicament, the injector module 105 is removed from the sensor module 100 while leaving the sensor module 100 in contact with the skin surface.

Decoupling the injector module 105 from the sensor module 100 enables a biometric parameter to be monitored (e.g. by the patient and/or a healthcare professional), both during the delivery of the medicament and after removal of the injector module. The biometric parameter may be, e.g., temperature, oxygen level, activity level (e.g., steps), heart rate, and/or blood pressure.

As described above, in various embodiments, the injector module 105 includes a coupling mechanism adapted to couple the injector module to the sensor module 110. For example, the injector module 105 may include a latch 130 adapted to mate with a recess 135 defined by the sensor module 110 and a push button 140 adapted to move the latch 130 between an engaged position and a disengaged position. Delivering the medicament may include pushing the push button 140 into a depressed position, which initiates insertion of the cannula 34 into the subcutaneous tissue. The injector module may include an injector timer, such that pushing the push button 140 into a depressed position starts the injection timer. Then, after a predetermined time in which the medicament is delivered, the push button moves to a released position. This moves the latch 130 to the disengaged position, thereby uncoupling, i.e., unlocking, a connection of the injector module 105 to the sensor module 110. The injector module 105 may be then be removed by the user, while the sensor module 110 remains in contact with the skin surface, thus enabling monitoring a biometric parameter or parameters after medicament delivery.

The teachings herein may be used to implement methods for delivering various medicaments, including but not limited to liquids, such as solutions, which may comprise any of adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, and/or brentuximab vedotin.

Each numerical value presented herein, for example, in a table, a chart, or a graph, is contemplated to represent a minimum value or a maximum value in a range for a corresponding parameter. Accordingly, when added to the claims, the numerical value provides express support for claiming the range, which may lie above or below the numerical value, in accordance with the teachings herein. Absent inclusion in the claims, each numerical value presented herein is not to be considered limiting in any regard.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention.

The features and functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A medicament delivery device comprising:
   a sensor module comprising:
      a sensor housing,
      at least one sensor disposed in the sensor housing, and
      an adhesive patch adapted for connecting the sensor module to a skin surface; and
   an injector module comprising:
      an injector module housing,
      a reservoir disposed in the injector module housing, the reservoir adapted to be filled with a medicament to be delivered to a patient,
      a cannula adapted to (i) fluidically connect with the reservoir and (ii) pass into a subcutaneous tissue, a needle initially disposed in a lumen defined by the cannula and adapted to pass into the subcutaneous tissue, and a coupling mechanism adapted to couple the injector module to the sensor module, the coupling mechanism comprising a latch, wherein the injector module is adapted to (i) be coupled to the sensor module during injection of the cannula and the needle into the subcutaneous tissue and during delivery of the medicament and (ii) be removed from the sensor module after the delivery of the medicament.

2. The medicament delivery device of claim 1, wherein the at least one sensor comprises at least one of a temperature sensor, an accelerometer, a gyroscope, a pulse oximeter, a blood pressure sensor, a hydration sensor, a pH sensor, glucose sensor, or a UV exposure sensor.

3. The medicament delivery device of claim 1, wherein the at least one sensor is disposed on a bottom surface of the sensor module and is configured to be in contact with the skin surface when the adhesive patch is connected thereto.

4. The medicament delivery device of claim 1, wherein the sensor module defines a recess adapted to mate with the latch.

5. The medicament delivery device of claim 1, wherein the coupling mechanism comprises a push button adapted to move the latch between an engaged position and a disengaged position.

6. The medicament delivery device of claim 5, wherein the push button extends through a portion of the injector module housing.

7. The medicament delivery device of claim 1, wherein the sensor housing of the sensor module defines a needle port.

8. A medicament delivery device of comprising:
a sensor module comprising:
a sensor housing, the sensor housing defining a needle port,
at least one sensor disposed in the sensor housing, and
an adhesive patch adapted for connecting the sensor module to a skin surface; and
an injector module comprising:
an injector module housing,
a reservoir disposed in the injector module housing, the reservoir adapted to be filled with a medicament to be delivered to a patient,
a cannula adapted to (i) fluidically connect with the reservoir, (ii) pass into a subcutaneous tissue, and (iii) pass through the needle port of the sensor module,
a needle initially disposed in a lumen defined by the cannula and adapted to pass into the subcutaneous tissue, and
a coupling mechanism adapted to couple the injector module to the sensor module,
wherein the injector module is adapted to (i) be coupled to the sensor module during injection of the cannula and the needle into the subcutaneous tissue and during delivery of the medicament and (ii) be removed from the sensor module after the delivery of the medicament.

9. A medicament delivery device comprising:
a sensor module comprising:
a sensor housing, the sensor housing defining a needle port,
at least one sensor disposed in the sensor housing, and
an adhesive patch adapted for connecting the sensor module to a skin surface; and
an injector module comprising:
an injector module housing,
a reservoir disposed in the injector module housing, the reservoir adapted to be filled with a medicament to be delivered to a patient,
a cannula adapted to (i) fluidically connect with the reservoir and (ii) pass into a subcutaneous tissue,
a needle initially disposed in a lumen defined by the cannula and adapted to (i) pass into the subcutaneous tissue and (ii) pass through the needle port, and
a coupling mechanism adapted to couple the injector module to the sensor module,
wherein the injector module is adapted to (i) be coupled to the sensor module during injection of the cannula and the needle into the subcutaneous tissue and during delivery of the medicament and (ii) be removed from the sensor module after the delivery of the medicament.

10. A method for delivering a medicament, the method comprising:
connecting to a skin surface a medicament delivery device comprising an injector module coupled to a sensor module comprising at least one sensor, wherein (i) the injector module comprises a reservoir containing the medicament, and (ii) the injector module comprises a coupling mechanism adapted to couple the injector module to the sensor module, the coupling mechanism comprising a latch;
delivering the medicament from the injector module into a subcutaneous tissue; and
after delivery of the medicament, removing the injector module from the sensor module while leaving the sensor module in contact with the skin surface.

11. The method of claim 10, wherein the injector module further comprises a cannula in fluidic communication with the reservoir, and delivering the medicament comprises passing the cannula into the subcutaneous tissue.

12. The method of claim 11, further comprising leaving the cannula in the subcutaneous tissue after delivery of the medicament.

13. The method of claim 11, wherein the injector module further comprises a needle disposed in a lumen in the cannula, and delivering the medicament comprises piercing the skin surface with the needle prior to passing the cannula into the subcutaneous tissue.

14. The method of claim 10, further comprising monitoring a biometric parameter with the sensor module.

15. The method of claim 14, wherein the biometric parameter is monitored after the injector module is removed.

16. The method of claim 14, wherein the biometric parameter comprises at least one of temperature, oxygen level, blood pressure, hydration, pH, glucose, or UV exposure.

17. The method of claim 10, wherein the sensor module defines a recess adapted to mate with the latch.

18. The method of claim 10, wherein the coupling mechanism comprises a push button adapted to move the latch between an engaged position and a disengaged position.

19. A method for delivering a medicament, the method comprising:
connecting to a skin surface a medicament delivery device of claim 8;
delivering the medicament from the injector module into a subcutaneous tissue; and
after delivery of the medicament, removing the injector module from the sensor module while leaving the sensor module in contact with the skin surface.

20. A method for delivering a medicament, the method comprising:

connecting to a skin surface a medicament delivery device of claim 9;
delivering the medicament from the injector module into a subcutaneous tissue; and
after delivery of the medicament, removing the injector module from the sensor module while leaving the sensor module in contact with the skin surface.

\* \* \* \* \*